(12) United States Patent
Rohner et al.

(10) Patent No.: US 11,457,998 B2
(45) Date of Patent: Oct. 4, 2022

(54) RECORDING DEVICE

(71) Applicant: Ivoclar Vivadent AG, Schaan (LI)

(72) Inventors: Gottfried Rohner, Altstätten (CH); Ronny Watzke, Feldkirch (AT); Theresa Sujata Maria Senti, Triesenberg (LI); Antonio Ferilli, Wängi (CH)

(73) Assignee: Ivoclar Vivadent AG, Schaan (LI)

( * ) Notice: Subject to any disclaimer, the term of this patent is extended or adjusted under 35 U.S.C. 154(b) by 33 days.

(21) Appl. No.: 17/097,664

(22) Filed: Nov. 13, 2020

(65) Prior Publication Data

US 2021/0059795 A1    Mar. 4, 2021

Related U.S. Application Data

(63) Continuation-in-part of application No. 16/320,820, filed as application No. PCT/EP2017/068753 on Jul. 25, 2017, now Pat. No. 10,863,904.

(30) Foreign Application Priority Data

Jul. 29, 2016 (EP) .................................. 16181975

(51) Int. Cl.
| | |
|---|---|
| *A61B 6/00* | (2006.01) |
| *A61C 9/00* | (2006.01) |
| *A61B 5/00* | (2006.01) |
| *A61B 6/14* | (2006.01) |
| *A61C 13/00* | (2006.01) |

(52) U.S. Cl.
CPC .......... *A61C 9/0046* (2013.01); *A61B 5/0086* (2013.01); *A61B 5/0088* (2013.01); *A61B 6/145* (2013.01); *A61C 13/0004* (2013.01); *A61B 5/6885* (2013.01)

(58) Field of Classification Search
CPC .. G01V 5/0016; H05H 9/048; A61B 1/00082; A61B 1/00172; A61B 5/0062; A61B 5/1079; A61B 5/682; A61C 9/0053
See application file for complete search history.

(56) References Cited

U.S. PATENT DOCUMENTS

| | | |
|---|---|---|
| 5,451,232 A | 9/1995 | Rhinehart et al. |
| 5,785,051 A | 7/1998 | Lipscher et al. |
| 7,751,606 B2 | 7/2010 | Luo et al. |
| 8,556,625 B2 | 10/2013 | Lovely |
| 9,414,750 B2 | 8/2016 | Lovely |
| 2005/0020910 A1 | 1/2005 | Quadling et al. |
| 2005/0123180 A1 | 6/2005 | Luo et al. |
| 2006/0241345 A1 | 10/2006 | Oishi |

(Continued)

FOREIGN PATENT DOCUMENTS

| | | |
|---|---|---|
| JP | 2000-126122 A | 5/2000 |
| WO | 02/00115 A1 | 1/2002 |

*Primary Examiner* — Dani Fox
(74) *Attorney, Agent, or Firm* — Ann M. Knab; Thad McMurray

(57) ABSTRACT

The invention relates to a recording device (10) comprising a scan head carrier (18) for moving the scan head (20) across a scan area (42) of a cavity, the scan area (42) extending around the scan head (20). The scan head guide (18) passes through the cavity towards the scan head (20). In particular, a control device (44) determines the shape of the cavity (40). A second extraoral scanning head (43) scans extraoral areas.

14 Claims, 2 Drawing Sheets

(56) References Cited

U.S. PATENT DOCUMENTS

| | | |
|---|---|---|
| 2007/0238981 A1 | 10/2007 | Zhu et al. |
| 2010/0222706 A1 | 9/2010 | Miyahara et al. |
| 2012/0056993 A1 | 3/2012 | Luqman |
| 2014/0276105 A1 | 9/2014 | De Brouchoven |
| 2014/0330133 A1* | 11/2014 | Stern .................... A61B 5/1076 600/509 |
| 2015/0350517 A1 | 12/2015 | Duret et al. |
| 2018/0192964 A1 | 7/2018 | Stalder et al. |

* cited by examiner

RECORDING DEVICE

CROSS-REFERENCE TO RELATED APPLICATIONS

This application claims priority to and is a continuation-in-part application of U.S. Ser. No. 16/320,820 filed Jan. 25, 2019, which is a National Stage application of International patent application PCT/EP2017/068753 filed on Jul. 25, 2017, which claims priority to European patent application No. 16181975.0 filed on Jul. 29, 2016, all the disclosures of which are incorporated herein by reference in their entirety.

FIELD OF THE INVENTION

The invention relates to a recording device as well as a method for operating a recording device.

BACKGROUND

It is known per se to arrange balloons that can be inflated around recording coils for evaluating measurement signals. Inflation is done through the balloon outlet which is also passed by the connecting lines for the sensor.

For the medical sector, such a solution can be found for example in DE 42 33 809 A1, but also for example in WO 2014/145058A1. Such solutions allow protection of sensitive sensor elements and are used, for example, to analyze auditory canals. Other related art includes US 20180192964, 20150350517, 20120056993, 20070238981, 20050020910, 20050123180, 9414750, 8556625, 7751606, all which are hereby incorporated by reference in their entirety.

In some cases, it is desirable to detect the internal structure of a partially fissured cavity. It has been suggested to use a stereometric method with scan heads separated by a given distance. The surface of the cavity to be scanned, the so-called scan area, is illuminated via an illumination device on the scan head and the scan area of the cavity is thus to be scanned.

However, despite the sophisticated scanner, the scan result is often unsatisfactory, so that it has been tried to further improve the scan head in a correspondingly expensive way. Nevertheless, the tests carried out so far in this respect, especially in the case of three-dimensionally complicated cavities, did not yield satisfactory results.

Nevertheless, in order to allow reasonably precise detection of the surface of the cavity, i.e. the scan area, it has already been suggested to work with different frequency ranges of the electromagnetic radiation. With a moist surface, for example, it can be advantageous to use visible light or UV light. On the other hand, the reflective properties of certain materials that can make up the cavity are better while using both ultrasound and X-rays.

A disadvantage herein resides that scanners having different frequency ranges are required to be provided, which overall makes the solution more expensive and sometimes no longer practicable.

These solutions are basically suitable for recording the static situation in the mouth. However, it lacks a solution for the functional impression, i.e. the impression of the oral situation taking into account deformation of mouth parts in different positions of the lower jaw to the upper jaw.

An attempt has been made to take an impression at different positions or at two different opening positions of the mouth. On the whole, the movement pattern is extremely complex due to the different anatomical features of the condylar joints and therefore not easily accessible to digitization.

SUMMARY OF THE INVENTION

Contrary to this, the object of the invention is to provide a recording device according to the claims as well as a method for operating a recording device according to the claims, which are also suitable for functional impressions, and, in any case, are significantly better than the recording devices of the prior art.

This object of the invention will be achieved according to the claims. Advantageous embodiments will arise from the subclaims.

According to the invention it is provided for the film-like material to spread in a balloon-like manner extending in particular across an alveolar ridge in the mouth of a patient, but also in the remaining oral cavity. A first scan head is inserted into this balloon. If the balloon is overpressurized, it is in contact with the scanning area, e.g. the edentulous alveolar ridge of the patient. The overpressure deforms soft tissue, while hard tissue such as existing teeth will not be deformed or will not really be deformed.

According to an alternate embodiment of the invention, no film-like or balloon material is used. The first scan head is inserted directly into the oral cavity, which is the scanning area, e.g. the edentulous alveolar ridge of the patient and the first scan head is able to scan the edentulous alveolar ridge to generate a 3D model of the scanned object.

The following elements discussed hereinafter apply to both above-mentioned embodiments, i.e., scanning devices with and without the film-like material.

Herein, the term scan head can be used to refer to any type of detection device that can be used directly or indirectly to generate a 3D model of the scanned object, e.g. a scan head using the Doppler effect, also known as OCT, electromagnetic radiation, e.g. visible or invisible light or X-rays, in particular an array of CCD chips, or ultrasound.

The extent of deformation depends on the overpressure applied. If overpressure is increased, stronger deformation occurs. It is intended to perform deformation using the appropriately selected overpressure, so that the scanning device will be able to detect whether soft tissue or hard tissue is present in the scan areas in question.

For this purpose, a pattern is preferably applied to the film-like material. The pattern can be seen from the first scan head and deformation due to pressurizing the film-like material can be detected.

According to the invention, it is provided for a second scan head to be spaced apart from the first scan head. Alternatively, it is also possible to create a scan head having several scan units, whereof one is arranged intraorally and the other one is arranged extraorally, so that the anatomical conditions in the mouth and outside the mouth can simultaneously be recorded. While the first scanning head is preferably located in the balloon or in the absence of the balloon, directly in the patient's mouth, the second scanning head is located outside the patient's mouth and is directed towards it. Alignment is such that the scanning axis is substantially aligned with the first scan head.

It is also possible to use different scanning procedures for the intraoral and extraoral scan heads. For example, a scan head with optical coherence tomography (OCT) could be used intraorally or as a first scan head, and a stereoscopic scan head could be used extraorally.

The detection area extends around this scanning axis, for example, such that at least the area of the patient's lips can be fully detected. It is also possible to significantly extend the scan area beyond this area, e.g. if the tragus or a marking element on the tragus and/or the bipupillary line is to be detected. If, for example, the second scanning head is positioned at a distance of 10 cm, a scanning angle of +/−45 degrees in each direction is sufficient to fully cover the patient's mouth.

According to the invention, the second scan head detects how the tissue surrounding the patient's mouth, especially the lips, deforms while the balloon is inflated, or alternatively, the tissue surrounding the patient's mouth, especially the lips in natural position without the use of a balloon.

The data obtained in this way, i.e. intraoral data based on the first scan head and extraoral data based on the second scan head, are only summarized electronically and the overall view subsequently shows how the patient's soft tissue is deformable in the mouth area, or alternatively shows the patient's soft tissue naturally, without deformation by a balloon.

Detection is preferably performed such that the balloon is inflated gradually and each of the corresponding 3D data are then acquired and, for example, are acquired at ⅓ nominal pressure, ⅔ nominal pressure or the full nominal pressure.

In an advantageous embodiment, it is provided for the pressure in the balloon to be slightly reduced, e.g. to 80% of the nominal pressure. The patient then has to perform functional movements, which compress the balloon. These movements are recorded by both scanning heads, or the resulting deformations of the soft tissue are recorded.

The intraoral or first scan head now records the points of movement of the pattern and the film-like tissue, the corresponding functional movements corresponding to the movements the patient makes.

It may eventually be necessary to regulate the pressure in the balloon, as air displacement imposed by the movement should be compensated.

According to the invention, the extraoral scanner preferably detects deformation of the soft tissue extraorally surrounding the mouth, or alternatively detects normal or natural position without any deformation of the soft tissue extraorally surrounding the mouth. In addition, the occlusal plane can also be detected, for example, by additionally detecting the pupils and a marker attached to the tragus. In this preferred embodiment, the detection areas of the extraoral scan head are appropriately selected so that the patient's eye/ear region can also be covered.

Based on the scan results of both scan heads during the functional movements, a digital functional model is then created which not only records the masticatory movements, but also the relevant area of the patient's head.

The occlusion plane can be used as a reference point for the tooth set-up based on the distance between the center of the lips and the tragi corresponding to the scanning of the extracorporeal scan head. Deformation of the lips and cheeks allows adaptation to the patient-specific anatomy during the fabrication of a prosthesis. The chin movements recorded can also be used to optimize the tooth set-up. Alternatively, natural position, without deformation of the lips and cheeks allows adaptation to the patient-specific anatomy during the fabrication of a prosthesis. The chin movements recorded can also be used to optimize the tooth set-up.

While the extraoral scan head can be used, according to the invention, to acquire and visualize the lip fullness, but also aesthetic lines such as the midline, canine line, smile line and lip closure line, the intraoral scanner acquires the functional margin and surface of the edentulous jaws.

The jaw relation can be determined by simultaneously scanning the upper and lower jaw. According to the invention, it is advantageous to work with variable pressure during the scanning process of both scan heads.

If the internal pressure in the balloon is reduced, the patient tends to reduce the mouth opening angle on his own. Corresponding movements of the patient's jaws relative to each other result in a change in the indentation pattern or the indentation depth of the film-like material or alternatively without deformation of a film, a change in the resulting scan.

For this purpose, an appropriate pattern can be applied to the film-like material. It is also possible to rather use a web or other flat material, which is suitable to be detected by at least one scan head.

According to the invention, realization of two scan heads also allows a three-dimensional image at least in the area that essentially extends between the scan heads, i.e. the area of the anterior/canine teeth as well as the corresponding mucous membranes and the lips.

While deformability measurement is preferably realized by using a single balloon, it is also possible in an alternative embodiment, to rather divide the balloon into a balloon having several chambers. They can be filled independently of each other, so that different mouth regions of the patient can each be filled with air.

According to the invention, it is provided to place the first scan head on a scan head carrier. The second scan head can also be mounted on the same scan head carrier or on a separate scan head carrier. The first scan head is provided for an all-round scan, i.e. for acquiring an image that spherically extends around the scan head. Thus, a scan area at least partially extends around the scan head.

A film-like material in the manner of a balloon is attached to the scanning area. It is overpressurized, which is possible, as the balloon forms a closed and deformable body.

The way in which the overpressure can be generated can, in any way, be adapted to the requirements. In this respect, a small hand pump is preferred, via which the operator can specifically generate a specified overpressure. Alternatively, it is also possible to implement a mechanical pump, in particular an automatically pressure-controlled pump. It can be connected to a manometer and/or a drain valve so that specific overpressure values can also be set.

In this embodiment, the balloon and the first scan head are intraorally arranged. It is to be understood that an equivalent can also be realized using a patient head model simulating the tissue of the patient.

Due to the overpressure, the film-like material deforms a soft tissue which is pressurized by the balloon.

Another scan head is provided spaced apart from but focused to the patient's mouth opening. This scanning head detects movements and/or natural positions with or without deformation, of the patient's lips, mouth and even the entire lower face. To facilitate detection, markings may be provided in and on the patient's mouth in any manner.

It is to be understood that any other markings, for example in the region of the tragi, and in any other places, are also possible.

It is also possible to configure the balloon or a separate chamber of the balloon such that it covers and fills the region of the oral vestibule. This requires an appropriate shape of the balloon, which follows the shape of the alveolar process. If necessary, a third scan head can also be formed here, or one of the two other scan heads can be moved to this position.

The film-like material is preferably realized as a disposable article and can also be produced at low cost.

Basically, a standard balloon with a corresponding imprint can be used to provide a sample. Such a balloon, while being orally accommodated, is pressure resistant in a suitable way, for example up to 1 bar, and then deforms the soft tissue to which it is attached without further intervention.

The detection spectrum of the scan heads can be the same or different. Any suitable electromagnetic radiation is possible herein, for example UV light, visible light, infrared light, X-rays. However, it is also possible to acquire data using ultrasound and, if required, a scan head can also be implemented using the Doppler Effect.

The technical measures for realizing scan heads are to be understood only as examples and are non-limiting.

According to the invention, it is also advantageous that the second scan head extraorally acquires the patient's image from the front when the balloon is being pressurized intraorally. The scan head recognizes where soft tissue is present and where deformation by hard tissue is prevented or limited, regardless of chewing movements. Alternatively, no balloon material is used and the second scan head extraorally acquires the patient's image from the front without a balloon being pressurized intraorally. The scan head recognizes where soft tissue is present and where deformation by hard tissue is prevented or limited, regardless of chewing movements.

It is preferable that a first scan head is mounted on a scan head carrier, the first scan head being designed for scanning an intraoral scan area which extends at least partially around the first scan head, and a second scan head is provided for scanning extraorally and which is spaced apart from the first scan head.

It is preferable that the intraoral scan area includes an edentulous alveolar ridge the extraoral scan area includes soft tissue extraorally surrounding a mouth.

It is preferable that the intraoral scan area includes an edentulous alveolar ridge and that scanning extraorally includes an extraoral area and an intraoral area.

It is preferable that soft tissue extraorally surrounding a mouth includes lip tissue and/or cheek tissue It is preferable that the scan head carrier has at least two scan head accommodations and that one scan head accommodation is always equipped with the first scan head and the other scan head accommodation can optionally be equipped with the second scan head.

It is preferable that the first scan head is essentially designed as an all-round scan head having an essentially spherical detection space and that the second scan head is designed as a directional scan head detecting significantly less than one hemisphere comprising a cone of approximately 120 degrees expansion.

It is preferable that the second scan head comprises a scanning axis that is substantially aligned towards the first scan head with a deviation of less than 30 degrees.

It is preferable that the first and second scan heads are each accommodated on a common scan head carrier in a spaced apart and precisely defined position in a scan head reception.

It is preferable that the recording device comprises a control and evaluation device detecting and evaluating scan results.

It is preferable that the control and the evaluation device of the recording device detects individual parts of the scanning area.

It is preferable that a digital model of a patient's head is produced based on a plurality of scanning operations of the first and/or the second scan head regarding anatomical conditions and respective tissue affected, which anatomical conditions and resilience of the respective tissue affected form the scanning region.

It is preferable that each scanning head provides for detection using UV light, visible light and/or infrared light and/or ultrasound and/or X-rays, separated by different spectra.

It is preferable that a control and evaluation device is provided in the recording device by which a bipolar line including at least one reference marker can be detected by the second scan head.

It is preferable that the recording device has a control and evaluation device by the use of which the anatomical conditions of lips and a surrounding region of a patient can be detected.

It is preferable that a method for operating a recording device comprising a first scan head which is mounted on a scan head carrier, the first scan head being designed for scanning an intraoral scan area which extends at least partially around the first scan head, and a second scan head for scanning extraorally and spaced apart from the first scan head comprises scanning the intraoral scan area and an extraoral scan area to provide scan data, and creating a digital functional model from the intraoral scan data and the extraoral scan data.

BRIEF DESCRIPTION OF THE DRAWINGS

Further details, advantages and characteristics of an example of the invention can be found in the following description, while making reference to the drawing.

DETAILED DESCRIPTION

Figure 1:
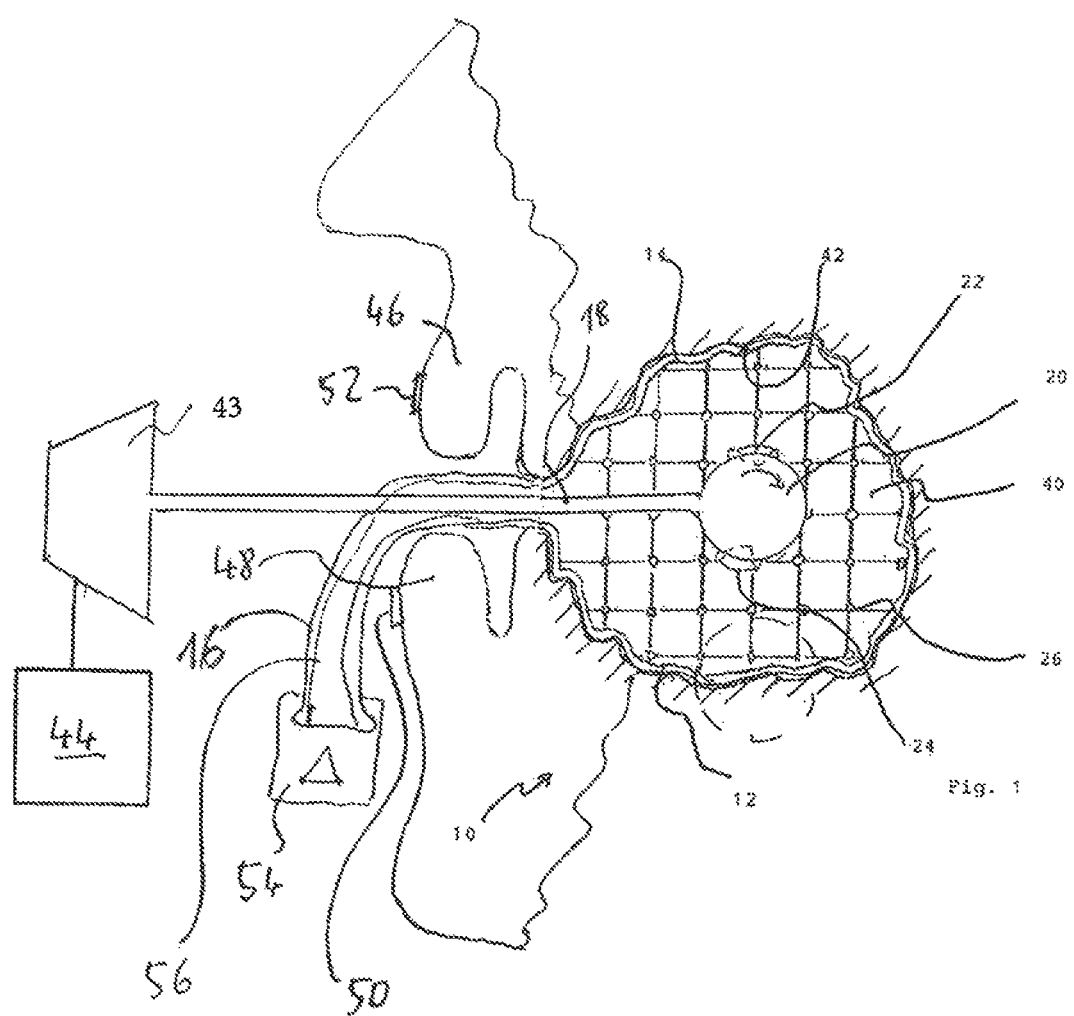
FIG. 1 shows a recording device according to the invention while being in use, in a first embodiment.

From FIG. 1, a schematic representation of a scanning device 10 according to the invention may be seen. It comprises a balloon 12 which consists of a balloon film 14 which forms the elastically stretchable material. The balloon 12 has a balloon outlet 16 in a manner known per se. A scan head carrier 18 passes through this outlet, holding a scan head 20 within the balloon and guiding it in a safe manner.

Several scanners are attached to the scan head 20, two of which scanners 22 and 24 being shown herein. A multitude of scanners can actually be provided, for example 100, while in case of a small number of scanners, it is preferred that they preferably are movably mounted at the scan head 20.

The scanners are to acquire the complete interior space of the balloon film 14. The balloon film 14 comprises a reference pattern 26 that, in the embodiment shown, is formed in the type of a web that can extend in even line spacing, or more preferably can extend unevenly across the balloon film. Especially if the line spacing is even, it is also possible to encode the lines, e.g. to dot them, i.e. to provide them with a unique dash-dot sequence, so that each line can be identified even if the position of the scan head changes.

The scan head carrier 18 is surrounded by a seal that seals the balloon outlet 16 against the ambient air.

A control device 44 is provided outside the balloon. In any case, this device evaluates the images acquired by the scanners and also controls an overpressure P which inflates the balloon 12.

Through inflation, the balloon film 14 closely and exactly follows the contour of a cavity 40. The reference pattern 26 thus extends along a scan area 42 in a deformed state. From the deformation of the reference pattern 26, the shape of the scan area can be calculated in detail according to the invention.

In an advantageous embodiment, the balloon 12 is inflated such that it completely abuts the inner surface of the cavity. By reducing the volume of the cavity, further increase in pressure occurs, which can be detected by the scan head 20.

The scan head 20 can be operated in any suitable wavelength range. Electromagnetic radiation such as light radiation, is conceivable, for which an additional light source is preferred, which illuminates the balloon's interior and is attached to the scan head 20. The use of X-rays or ultrasound is also possible instead or in addition.

In another embodiment it is conceivable to first insert a scanning accessory means which is transparent to the scanning radiation, into the cavity and to then cure it.

The scanning accessory means has an insertion aperture for a scan head. It is cured in cavity 40, thereby deforming the reference pattern applied to the surface of the scanning accessory means. Subsequent to at least being partially cured, it is removed—if required by elastic compression or by opening the cavity—and subsequently the scan head is inserted into the scanning accessory means and the surface of the scanning accessory means is scanned from the inside.

According to the invention, realization of a second scan head 43 is provided extraorally, in addition to the first scan head 20. In the example as illustrated, the second scan head 43 is mounted on the same scan head carrier 18. Both scan heads are mounted externally or are supported on the patient's mouth.

It is to be understood that instead a stationary holder can also be provided, which carries and supports the first and/or second scan head 43, so that the patient must actively approach this arrangement to enable scanning.

Both scanning heads are electrically connected and are also connected from the control towards a control device 44 that starts and runs the scanning processes either automatically or after intervention of the operator, but also evaluates the images acquired, and combining the results obtained in a way appropriate to each individual patient.

The scan head 43 is aligned towards the scan head 18, acquiring the image of the closed/open/semi-open mouth of the patient, especially including the lips 46 and 48, but preferably also beyond that, for example up to the region of the ears of the patient.

The angle of coverage can be broadly be adapted according to the requirements. It is also possible to connect a focusing device upstream of the second scan head, which, in the manner of a variable wide-angle lens, provides the necessary image section.

Preferably, marking elements 50 and 52 are attached to the tragus, on the lips and/or in the alveolar region when the mouth is half-opened, the positions of which are detectable by the second scan head 43.

In any case, the second scan head 43 also records functional movements performed by the patient, thus enabling a functional scan to provide dynamic data for the prosthesis/prostheses to be manufactured.

In order to provide the desired overpressure, a pressure source 54 comprising a pressure hose 56 is provided, which is connected to the balloon 12 and pressurizes it so that, in the oral cavity, abuts against the tissue located therein, the so-called scan area.

According to the invention, different pressure levels of the balloon are now being acquired by the scan heads 20 and 43. Alternatively, the patient can be asked to compress the balloon 12 by closing the mouth.

This also results in deformation of the adjacent soft tissue and thus the possibility of analyzing and determining the tissue distribution according to the invention.

Figure 2:
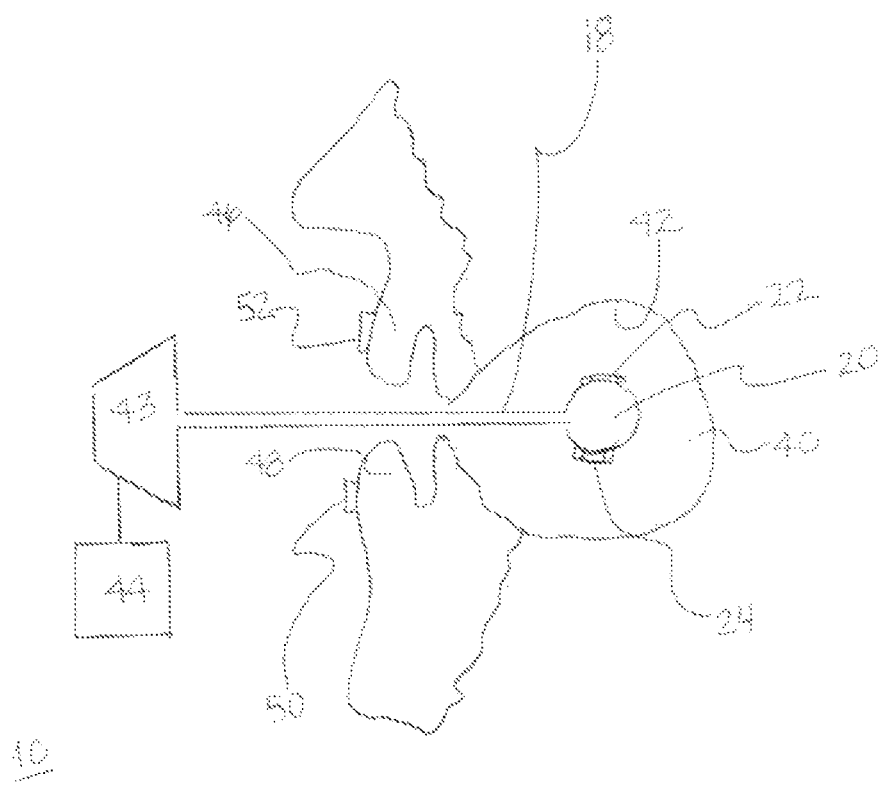
FIG. 2 shows a recording device without a film-like material according to an embodiment of the invention.

From FIG. 2, a schematic representation of a scanning device 10 according to the invention may be seen. It includes a scan head carrier 18 holding a scan head 20 within the oral cavity 40.

Several scanners are attached to the scan head 20, two of which scanners 22 and 24 being shown herein. A multitude of scanners can actually be provided, for example 100, while in case of a small number of scanners, it is preferred that they preferably are movably mounted at the scan head 20.

The scanners are to acquire the complete or substantially compete interior space of the oral cavity 40.

A control device 44 is provided outside the oral cavity 40. In any case, this device evaluates the images acquired by the scanners.

The scan head 20 can be operated in any suitable wavelength range. Electromagnetic radiation such as light radiation, is conceivable, for which an additional light source is preferred, which illuminates the interior and is attached to the scan head 20. The use of X-rays or ultrasound is also possible instead or in addition.

In another embodiment it is conceivable to first insert a scanning accessory means which is transparent to the scanning radiation, into the cavity and to then cure it.

The scanning accessory means has an insertion aperture for a scan head. It is cured in cavity 40. Subsequent to at least being partially cured, it is removed—if required by elastic compression or by opening the cavity—and subsequently the scan head is inserted into the scanning accessory means and the surface of the scanning accessory means is scanned from the inside.

According to the invention, realization of a second scan head 43 is provided extraorally, in addition to the first scan head 20. In the example as illustrated, the second scan head 43 is mounted on the same scan head carrier 18. Both scan heads are mounted externally or are supported on the patient's mouth.

It is to be understood that instead a stationary holder can also be provided, which carries and supports the first and/or second scan head 43, so that the patient must actively approach this arrangement to enable scanning.

Both scanning heads are electrically connected and are also connected from the control towards a control device 44 that starts and runs the scanning processes either automatically or after intervention of the operator, but also evaluates the images acquired, and combining the results obtained in a way appropriate to each individual patient.

The scan head 43 is aligned towards the scan head 18, acquiring the image of the closed/open/semi-open mouth of the patient, especially including the lips 46 and 48, but preferably also beyond that, for example up to the region of the ears of the patient.

The angle of coverage can be broadly be adapted according to the requirements. It is also possible to connect a focusing device upstream of the second scan head, which, in the manner of a variable wide-angle lens, provides the necessary image section.

Preferably, marking elements 50 and 52 are attached to the tragus, on the lips and/or in the alveolar region when the mouth is half-opened, the positions of which are detectable by the second scan head 43.

In any case, the second scan head 43 also records functional movements performed by the patient, thus enabling a functional scan to provide dynamic data for the prosthesis/prostheses to be manufactured.

The invention claimed is:

1. A recording device arrangement comprising
a first scan head which is mounted on a scan head carrier, the first scan head being designed for scanning an intraoral scan area which extends at least partially around the first scan head, and
a second scan head for scanning extraorally and spaced apart from the first scan head,
wherein the first scan head is an all-around scan head having a spherical detection space, and
wherein the second scan head is a directional scan head detecting less than one hemisphere.

2. The recording device arrangement according to claim 1,
wherein the intraoral scan area comprises an edentulous alveolar ridge, and
wherein scanning extraorally comprises scanning soft tissue extraorally surrounding a mouth.

3. The recording device arrangement according to claim 1,
wherein the intraoral scan area comprises an edentulous alveolar ridge, and
wherein scanning extraorally comprises scanning an extraoral area and an intraoral area.

4. The recording device arrangement according to claim 1,
wherein soft tissue extraorally surrounding a mouth comprises lip tissue and/or cheek tissue.

5. The recording device arrangement according to claim 1,
wherein the scan head carrier has at least two scan head accommodations, and
wherein one scan head accommodation is always equipped with the first scan head and the other scan head accommodation can optionally be equipped with the second scan head.

6. The recording device arrangement according to claim 1,
wherein the less than one hemisphere comprises a cone of approximately 120 degrees expansion.

7. The recording device arrangement according to claim 1,
wherein the second scan head comprises a scanning axis that is substantially aligned towards the first scan head with a deviation of less than 30 degrees.

8. The recording device arrangement according to claim 1,
wherein the first and second scan heads are each accommodated on a common scan head carrier in a spaced apart and precisely defined position in a scan head reception.

9. The recording device arrangement according to claim 1,
wherein the recording device comprises a control and evaluation device detecting and evaluating scan results.

10. The recording device arrangement according to claim 9,
wherein the control and the evaluation device of the recording device detects individual parts of the scanning area.

11. The recording device arrangement according to claim 1,
wherein a digital model of a patient's head is produced based on a plurality of scanning operations of the first and/or the second scan head regarding anatomical conditions and respective tissue affected, which anatomical conditions and resilience of the respective tissue affected form the scanning region.

12. The recording device arrangement according to claim 1,
wherein each scanning head provides for detection using UV light, visible light and/or infrared light and/or ultrasound and/or X-rays, separated by different spectra.

13. The recording device arrangement according to claim 1,
wherein a control and evaluation device are provided in the recording device by which a bipolar line including at least one reference marker can be detected by the second scan head.

14. The recording device arrangement according to claim 1,
wherein the recording device has a control and evaluation device by the use of which the anatomical conditions of lips and a surrounding region of a patient can be detected.

* * * * *